(12) United States Patent
Voisard et al.

(10) Patent No.: US 9,956,014 B2
(45) Date of Patent: May 1, 2018

(54) METHOD FOR JOINING TWO OR MORE SEGMENTS OF A SURGICAL IMPLANT

(75) Inventors: Cyril Voisard, Langendorf (CH); Robert Frigg, Langendorf (CH); Goetz Thorwarth, Langendorf (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 1003 days.

(21) Appl. No.: 13/233,702

(22) Filed: Sep. 15, 2011

(65) Prior Publication Data
US 2012/0239036 A1 Sep. 20, 2012

Related U.S. Application Data

(60) Provisional application No. 61/384,537, filed on Sep. 20, 2010.

(51) Int. Cl.
| | |
|---|---|
| *A61B 17/80* | (2006.01) |
| *A61B 17/68* | (2006.01) |
| *A61B 17/72* | (2006.01) |
| *A61F 2/30* | (2006.01) |

(52) U.S. Cl.
CPC .............. *A61B 17/80* (2013.01); *A61B 17/68* (2013.01); *A61B 17/72* (2013.01); *A61F 2002/30454* (2013.01); *A61F 2002/30457* (2013.01)

(58) Field of Classification Search
CPC ......... A61B 17/866; A61F 2002/30454; A61F 2002/30457
USPC ................. 606/298, 70; 428/635; 228/234.3
See application file for complete search history.

(56) References Cited

U.S. PATENT DOCUMENTS

| | | | |
|---|---|---|---|
| 4,752,295 A | 6/1988 | Frey et al. | |
| 5,381,944 A * | 1/1995 | Makowiecki et al. | ..... 228/124.5 |
| 5,899,939 A * | 5/1999 | Boyce et al. | ............... 623/16.11 |
| 6,123,731 A * | 9/2000 | Boyce et al. | ............... 623/23.63 |
| 6,572,379 B1 * | 6/2003 | Sears et al. | .................... 434/234 |
| 6,736,942 B2 * | 5/2004 | Weihs et al. | ............. 204/192.12 |
| 8,128,628 B2 | 3/2012 | Freid et al. | |
| 2004/0243241 A1 * | 12/2004 | Istephanous et al. | ..... 623/17.14 |
| 2005/0082343 A1 * | 4/2005 | Wang et al. | .................. 228/115 |
| 2006/0247638 A1 * | 11/2006 | Trieu et al. | ..................... 606/69 |
| 2007/0202351 A1 | 8/2007 | Justin et al. | |
| 2007/0225707 A1 * | 9/2007 | Wisnewski et al. | ............ 606/61 |
| 2008/0093418 A1 * | 4/2008 | Weihs et al. | .................. 228/101 |
| 2008/0272181 A1 * | 11/2008 | Wang et al. | ............... 228/234.3 |

(Continued)

FOREIGN PATENT DOCUMENTS

| | | |
|---|---|---|
| CN | 1886746 | 11/2008 |
| CN | 101569554 | 11/2008 |

(Continued)

*Primary Examiner* — Jan Christopher Merene
*Assistant Examiner* — Atiya Mahmud
(74) *Attorney, Agent, or Firm* — Fay Kaplun & Marcin, LLP

(57) ABSTRACT

A method for joining two or more segments of a bone implant comprises the steps of placing a plurality of thin layers of an intermetallic material between first and second segments of the bone implant and applying a mechanical load to the plurality of layers. In a subsequent step, the plurality of layers are ignited by applying an external activation energy thereto, the ignition heating the plurality of layers to a reaction temperature and causing the segments to become affixed to one another after cooling.

14 Claims, 2 Drawing Sheets

(56) References Cited

U.S. PATENT DOCUMENTS

| | | | |
|---|---|---|---|
| 2009/0065554 A1* | 3/2009 | Heerden et al. | 228/44.3 |
| 2009/0143780 A1 | 6/2009 | Gabele et al. | |
| 2009/0275947 A1* | 11/2009 | Graham et al. | 606/71 |
| 2010/0038409 A1* | 2/2010 | Wilden et al. | 228/121 |
| 2010/0124669 A1* | 5/2010 | Lee et al. | 428/660 |
| 2010/0262194 A1* | 10/2010 | Wagner et al. | 606/286 |
| 2012/0071875 A1* | 3/2012 | Von Wieding et al. | 606/71 |

FOREIGN PATENT DOCUMENTS

| | | |
|---|---|---|
| EP | 2 085 039 | 8/2009 |
| EP | 2 113 216 | 11/2009 |
| JP | 2005-515823 | 6/2005 |
| WO | 2010/059866 | 5/2010 |

* cited by examiner

METHOD FOR JOINING TWO OR MORE SEGMENTS OF A SURGICAL IMPLANT

PRIORITY CLAIM

The present application claims priority to U.S. Provisional Application Ser. No. 61/384,537 entitled "Method for Joining Two or More Segments of a Surgical Implant" filed on Sep. 20, 2010, the entire disclosure of which is hereby incorporated by reference.

FIELD OF THE INVENTION

The present invention generally relates to a method for joining two or more segments of a surgical implant to one another. In particular, the present invention relates to a multi-part implant (e.g., an intramedullary nail, a screw or osteosynthesis plate) formed of several components connected to one another by a metallurgical weld.

BACKGROUND OF THE INVENTION

Intramedullary nails for the stabilization of fractures, e.g. of the proximal femur, sometimes employ titanium alloys. However the strength of titanium alloys is limited and does not allow for smaller diameter intramedullary nails, especially for smaller diameter proximal portions of the intramedullary nail. In order to overcome this deficiency, high strength materials are sometimes used for the construction of the intramedullary nail. Specifically, present devices are directed to two body portions mechanically connected to one another. However, such devices often lose holding strength within the bone as the mechanical connection weakens over time. Furthermore, frictional movement of the two body portions relative to one another causes galvanic corrosion.

Thus, in present devices, additional strength is needed to ensure that an implant can cope with the high dynamic loads and loading cycles experienced in the body as well to avoid fretting corrosion.

SUMMARY OF THE INVENTION

The present invention relates to a method for joining two or more segments of a bone implant and comprises the steps of placing a plurality of thin layers of an intermetallic material between first and second segments of the bone implant and applying a mechanical load to the plurality of layers. In a subsequent step, the layers are ignited by applying an external activation energy thereto, the ignition heating the plurality of layers to a reaction temperature and causing the segments to become affixed to one another after cooling.

In a special embodiment, the plurality of thin layers of an intermetallic material are configured with a negative heat of mixing.

In a special embodiment, the step of igniting the plurality of layers may trigger an exothermic self-propagating inter-diffusion reaction.

In a special embodiment the intermetallic material is chosen from the group consisting of Ti/Al, Ni/Al, Ti/Si, Zr/Al, Ti/N, and Ti5Si3. Preferably, alternate layers of the plurality of layers comprise different intermetallic material selected from the chosen group.

In a further embodiment, the bone implant comprises between 500 and 5000 layers.

In again a further embodiment, each thin layer has a thickness of at least 15 nm, preferably at least 20 nm.

In another embodiment, each of the thin layers has a thickness of no more than 50 nm, preferably no more than 40 nm.

In yet another embodiment, a first one of the layers is separated from a second one of the layers by a spacer layer. This configuration prevents intermixing of the single thin layers. This configuration also ensures better material separation at room temperature and maximizes the formation enthalpy released in the ignition process.

In again another embodiment, the mechanical load is at least 70 MPa and preferably at least 100 MPa. This load is useful for establishing a sufficient contact area depending on the elasticity and roughness of the first and second segments to be joined. Without a sufficient load, only a small amount of joining would occur and have only weak mechanical properties.

In still another embodiment, the negative heat of mixing is at least 15 kJ/mol, preferably at least 36 kJ/mol.

In a further embodiment, the reaction temperature is above 800° C., preferably above 1200° C.

In again a further embodiment, the first and second segments comprise a substrate material selected from the group consisting of Ti, Ti alloys, stainless steel, Co alloys, glass metals, Mg alloys and ceramic/metal-composites.

In still a further embodiment, the method further comprises the step of applying a solder to join the first and second segments to one another.

In another embodiment, the solder is one of Al, AuSn, AgIn or AuGe.

In yet another embodiment, the first segment is further joined to the second segment by mechanical locking.

In again another embodiment, the surgical implant is one of a bone plate and an intramedullary nail.

In a further embodiment, the plurality of thin layers is applied as a coating on at least one of the first and second segments.

In a further embodiment, a foil is formed from the plurality of layers and is placed between the first and second segments of the bone. Preferably, a solder is applied to the foil before applying the mechanical load.

According to a further aspect of the invention, there is provided a surgical implant obtained by the method according to the invention.

According to another aspect of the invention, a modular multiple piece bone implant kit is provided, wherein the kit can be assembled by the manufacturer or preoperatively or intra-operatively according to the patient's need from a limited number of segments available in the kit.

According to again another aspect of the invention, the kit further comprises a foil having a plurality of thin layers of an intermetallic material with a negative heat of mixing. In a special embodiment of the kit, each of at least two segments is each made from a different material.

BRIEF DESCRIPTION OF THE DRAWINGS

Several embodiments of the present invention will be described in the following by way of example and with reference to the accompanying drawings in which.

DETAILED DESCRIPTION OF THE INVENTION

The present invention relates to a system and method for the construction of a multi-part bone fixation device in a manner selected to increase and/or maximize a holding strength of each part of the bone fixation device when brought into contact with one another. Specifically, an exemplary embodiment of the present is directed to a bone fixation device (i.e., an intramedullary nail, a bone screw, an osteosynthetic bone plate, etc.) formed of several components formed of different materials bonded to one another via a metallurgical weld. The exemplary embodiment according to the present invention also permits a user to select materials with different properties (e.g., rigidity, flexibility, surface type, etc.) for different portions of the bone fixation device to fine-tune the mechanical properties of respective portions of the bone fixation device to the requirements of a particular procedure. In an exemplary embodiment, body portions may be attached to one another during manufacturing, pre-operatively or, in select cases, in-vivo. For example, the physician or other user may configure the bone implant with added strength on a first end of the bone implant and added flexibility on a second end. Furthermore, the exemplary system according to the present invention offers the possibility to limit size variations of different components of the bone implant (i.e., components formed of different materials) to only targeted parts of the implant without having to account for expensive manufacturing limitations. For example, by using high strength materials for only required portions of the bone implant, the overall size of the bone implant may be reduced, facilitating insertion. Building up the bone implant with either a standard or a non-standard shape offers the production of a large variety of possible configurations in a cost effective way. It is noted that although the present invention is described with respect to particular components and configurations, any number of shapes of bone fixation device components may be employed without deviating from the spirit and scope of the present invention.

Figure 1:
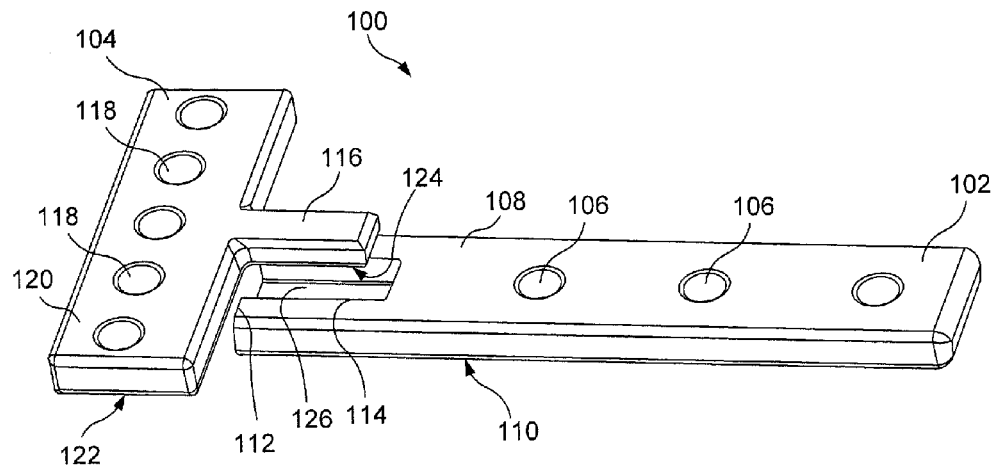
FIG. 1 depicts a partially exploded view of a bone fixation device according to a first embodiment of the present invention.
Figure 2:
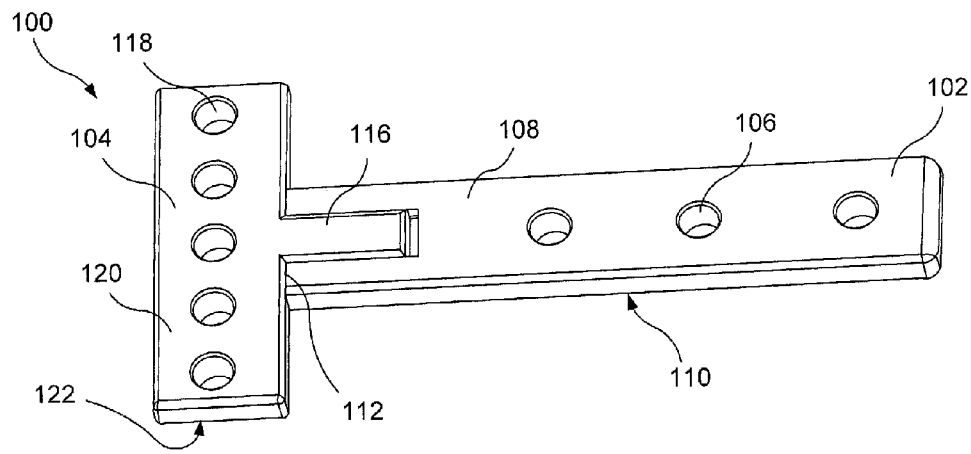
FIG. 2 depicts a second perspective view of the bone fixation device of FIG. 2.

A bone fixation system 100 as depicted in FIGS. 1-2 comprises first and second bone plates 102, 104 configured to be attached to one another as described hereinafter. The first bone plate 102 is formed as an elongated element having a substantially rectangular cross section and configured for placement over an elongated portion of a bone. It is noted, however, that the first bone plate 102 may be formed with any other shape suited to a particular portion of bone over which the first bone plate 102 is to be placed. Specifically, the first bone plate 102 may be configured for placement over one of a right and left bone portion and may be sized to conform to the requirements of a particular bone. The first bone plate 102 comprises a plurality of first plate holes 106 extending therethrough from a proximal surface 108 to a distal surface 110 configured to face the bone in an operative configuration. A first end 112 of the first bone plate comprises a recess 114 extending distally from the proximal surface 108 to a predetermined depth smaller than a thickness of the first bone plate 102. The recess 114 has a substantially rectangular cross-sectional shape and is configured and dimensioned to receive a protrusion 116 provided on the second bone plate 104. The second bone plate 104 is also formed with an elongated body portion having a plurality of second screw holes 118 extending therethrough from a proximal surface 120 to a distal surface 122, the second screw holes 118 being longitudinally aligned along a longitudinal axis of the second bone plate 104. A protrusion 116 extends out of the second bone plate 104 at an angle substantially perpendicular to the longitudinal axis of the second bone plate 104. The protrusion 116 extends distally from the proximal surface 120 to a predetermined depth smaller than or equal to the depth of the recess 114 so that a distal face 124 of the protrusion 116 is separated from a distal surface of the elongated portion of the second bone plate 104. As those skilled in the art will understand, this configuration allows proximal surfaces 108, 120 of the first and second bone plates 102, 104 to be seated in alignment with one another in the same plane when the protrusion 116 is seated in the 114. In an exemplary embodiment, at least a distal wall 126 of the recess 114 is coated with a plurality of layers of a material selected to permit reactive welding with the protrusion 116. In another embodiment, the entire surface of the recess 114 is coated with the plurality of layers of the material. At least the distal wall 124 of the protrusion 116 is also coated with a corresponding plurality of layers of the material. In another embodiment, sidewalls of the protrusion configured to contact the recess 114 in an operative configuration may also be coated with the plurality of layers of the material. In another embodiment, only the recess 114 is coated with the plurality of layers of the material. In yet another embodiment, only the protrusion 116 is coated with the plurality of layers of the material. In still another embodiment, both the recess and the protrusion 116 are coated with the plurality of layers of the material.

The layers may be formed of one or more materials deposited over one another. In one embodiment, a first layer of AuSn may be deposited over a predetermined portion of the bone fixation system 100. A layer of NiAl may be deposited over the AuSn layer and followed by another AuSn layer so that the NiAl layer is encased within the AuSn layers. As those skilled in the art will understand, having only the AuSn layers exposed provides for a stronger weld due to the wetting properties of AuSn. In another embodiment of the invention, another intermediate layer may be provided between the AuSn and NiAl layers. As will be described in greater detail later on, the above-recited layers may be welded via reactive welding or another welding technique. The exemplary multi-layer coating according to the present invention permits welding to be performed at reduced heat levels so that heating of the core of the bone fixation system 100 is limited while the surface portions of the bone fixation system 100 are elevated to a temperature at which the AuSn may be wetted. In contrast, conventional welding may require more significant heating which could raise the temperature of a substantial portion of a body of a device to levels which could alter the characteristics of the core changing the properties of the underlying material in undesirable ways. That is, this method allows the core of the bone fixation system 100 to remain substantially cool during welding preserving the material properties of the first and second bone plates 102, 104 during the welding.

Each of the first and second bone plates 102, 104 may be selected to have material properties, geometries (e.g., shape, size, thickness, etc.) and surface types conforming to the requirements of a particular procedure. For example, a polymer or a metal such as Titanium or a Titanium alloy may be used to impart flexibility to one of the first and second bone plates 102, 104. Chromium or another metal may be used to impart stiffness. In one embodiment, the first body portion 102 may be formed of Titanium and the second body portion 104 may be formed of Chromium so that the strength of the wider second body portion 104 is sufficient to withstand forces exerted thereon after implantation, as those skilled in the art will understand. In a first exemplary embodiment, each of the first and second bone plates 102, 104 may be formed of the same material. In another exemplary embodiment, the first and second bone plates 102, 104 may be formed of different materials. As will be described in greater detail with respect to the exemplary method of the invention, the selected materials for the first and second bone plates 102, 104 may make one type of welding preferable for connecting the bone plates 102, 104 to one another. The first and second bone plates 102, 104 may also be provided with surface treatments to roughen an outer surface thereof to enhance bonding as would be understood by those skilled in the art. In yet another embodiment (not shown), one or both of the first and second bone plates 102, 104 may be porous (i.e., to stimulate bone ingrowth), non-porous, coated or non-coated. The surfaces of the first and second bone plates 102, 104 may also be pretreated (e.g., via sputter-wave treatment, etc.) to enhance the weld.

In accordance with an exemplary method, the protrusion 116 is brought into a seated configuration in the recess 114 as shown in FIG. 2. Welding may then be performed by using an ignition technique such as a spark discharge to cause a localized heat production sufficient to cause the protrusion 116 to be welded in place in the recess 114. The welding procedure may be performed during manufacturing, pre-operatively or intra-operatively so that a physician may select first and second bone plates 102, 104 from a kit comprising a plurality of additional bone plates, the selected bone plates having the properties required for a particular procedure.

Figure 3:
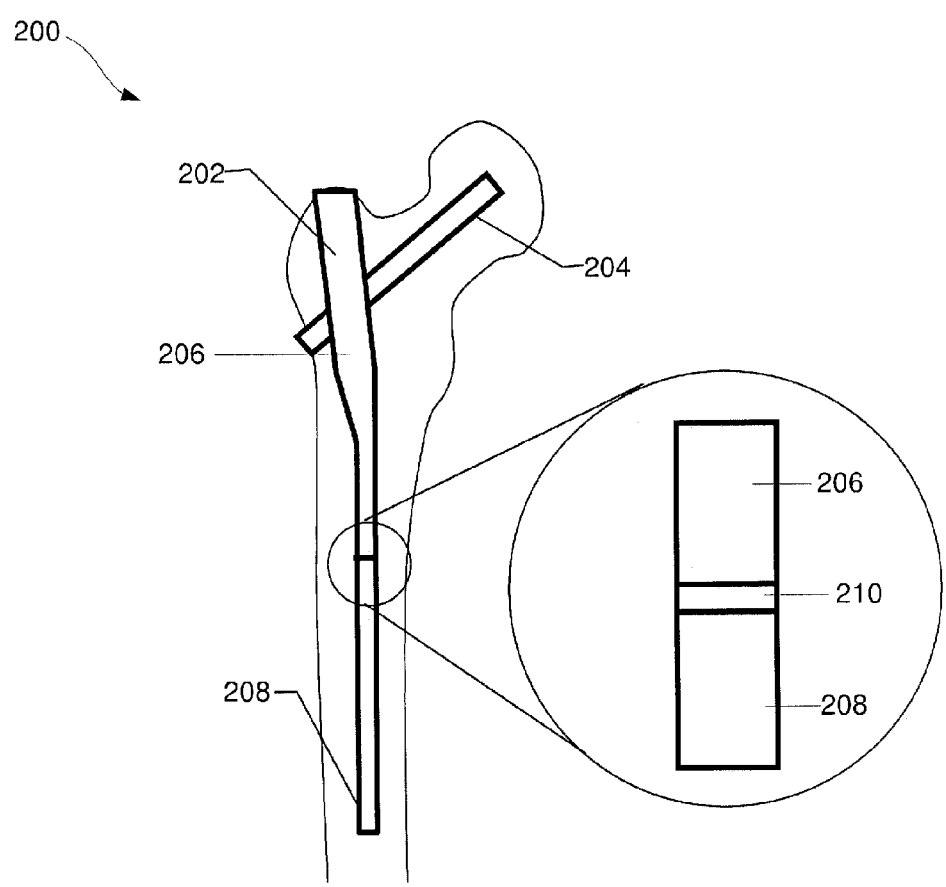
FIG. 3 depicts a first perspective view of a bone fixation device according to a second embodiment of the present invention.

As depicted in FIG. 3, a bone fixation system 200 according to a second embodiment of the present invention comprises an intramedullary nail 202 having a bone screw 204 extending therethrough at a predetermined angle with respect to a longitudinal axis of the intramedullary nail 202. A proximal portion 206 of the intramedullary nail is formed with a thickness greater than a thickness of a distal portion 208, the thickness being selected to permit insertion into an epiphysis or metaphysis and shaft of a bone, respectively. The proximal portion 206 is formed of a bimetallic material such as CoCrMo while the distal portion 208 is formed of TiAlNb, the proximal and distal portions 206, 208 being attached to one another by a safe thread design, as those skilled in the art will understand. The selected materials for the proximal and distal portions 206, 208 permit the use of a reduced diameter distal portion 208 while maintaining a rigidity of the proximal portion 206. FIG. 2 depicts the intramedullary nail 202 after the proximal and distal portions 206, 206 have been welded to one another with a joint 210 provided therebetween. In one exemplary embodiment, a surface area of the joint 210 may be approximately 1 cm$^2$, with the joint 210 angled as necessary to ensure at least a minimum required surface area. Specifically, if a diameter of the proximal and distal portions 206, 208 at the joint 210 is not sufficient to yield the minimum required surface area, the joint 210 may be angled at any angle relative to a longitudinal axis of the intramedullary nail 202 to increase the surface area. As those skilled in the art will understand, having a joint portion 210 with a predetermined surface area ensures a proper fixation of the proximal portion 206 to the distal portion 208 without a loss of strength when subjected to high dynamic mechanical stresses. A joining technique used for the intramedullary nail 202 must not alter the properties of both the CoCrMo and TiAlNb components. In an exemplary embodiment, the joint portion 210 comprises a multilayer foil consisting of 1000 periods of Ni/Al sublayers placed into a joint region between a distal end of the proximal portion 206 and a proximal end of the distal portion 208 with an AuSn solder foil. It is noted that although the joint portion 210 of the present embodiment is depicted in a particular location along a length of the intramedullary nail 202, any other joint region may be selected without deviating from the scope of the invention. In one example, the joint region may be selected so that a mechanical load placed upon the joint site is minimized when subjected to normal stresses when implanted within a bone.

Once the Ni/Al sublayers have been placed in the joint portion 210, a predetermined pressure is applied thereto. In one example, the load is greater than 70-100 MPa. The Ni/Al sublayers are then ignited and a solder is uniformly dispersed thereover and caused to interdiffuse into proximal and distal ends of the joint portion 201. The result is a joint portion 210 that is sufficiently stable to withstand expected mechanical loads at the joint region.

In a first variation of the bone fixation system 200, the proximal portion 206 of the intramedullary nail 202 is made of CoCrMo and is connected to the distal portion 208 formed of TiNbTaZr by a safe thread design. The proximal and distal portions 206, 208 may be welded by reactive welding. The bone screw 204 may be a telescoping hip screw formed of CoCrMo. A gliding surface of the bone screw 204 may be coated with diamond-like carbon. After insertion of the bone screw 204 into a respectively configured hole (not shown) extending through the proximal portion 206, welding is accomplished via ignition of a Ti/Ni multilayer stack via a laser pulse at a joining pressure of 100 MPa, as those skilled in the art will understand. The multilayer stack may have, for example, 500 stack elements with individual layers having a thickness of approximately 20 nm.

In another embodiment of the present invention, a bone plate (not shown) is formed of a TiAlNb alloy and has a shape and size suitable for a predetermined procedure. The bone plate is made up of, for example, two segments joined together. The bone plate is similar to that shown in FIG. 1, with the exception of a construction thereof. Specifically, the bone plate (not shown) comprises a first segment (not shown) having a plurality of recesses and a second segment (not shown) having a plurality of protrusions. In another embodiment of the invention, a single segment having one or more recesses and protrusions may be provided. The recesses and protrusions feature contact patches. The contact patches feature a multilayer arranged to allow the first and second segments to be welded together. The multilayer is formed of a 200-micrometer thick Ni/Al multilayer wherein a thickness of individual layers of the multilayer is approximately 20 nm with 5000 periods of Ni/Al, as those skilled in the art will understand. This multilayer is deposited by physical vapor deposition ("PVD") using DC sputtering with an argon pressure of $1\times10^{-3}$ mbar and a base vacuum of $1\times10^{-8}$ mbar. The deposition completely coats exposed surface areas of the first and second segments to form contact patches, wherein the surface areas may range from 1 mm$^2$ to 1 cm$^2$.

In another exemplary embodiment of reactive multilayer welding, first and second surfaces of first and second bone plate segments may be placed in a vacuum of $1\times10^{-5}$ mbar or stronger. Oxidized portions on the first and second surfaces are removed via RF sputtering in an Argon or Argon/Hydrogen plasma with an RF self-bias of −600V for approximately 60 minutes, as those skilled in the art will understand. A multilayer system is then deposited onto one or both of the first and second surfaces via magnetron sputtering (e.g., Argon gas at a pressure of $5e^{-3}$ mbar). In an exemplary embodiment a first layer of 10 nm Ti may be followed by a layer of 1 µm Cu and a final outer layer of 200 nm Au. The first and second surfaces may then be removed from the vacuum chamber. A 20 µm thick Au20Sn braze foil may then be placed on one or both of the first and second surfaces. A 40 µm thick Ni/Al intermetallic foil is then placed on one of the first and second surfaces. In one embodiment, each of the individual layers of the intermetallic foil may be approximately 30 nm thick. The first and second surfaces are then brought into a contacting configuration and a pressure of approximately 20 MPa is applied thereto. An electric spark is then applied to ignite the intermetallic layer, bonding the first and second surfaces to one another.

A modular bone plate can subsequently be fabricated by joining the first and second segments having contact patches by placing a protrusion of the second segment into a recess of the first segment under a load of approximately 100 MPa. A spark or laser pulse may then be applied to the multilayer to cause a rapid self-propagating reaction (interdiffusion and freeing of bond enthalpy) along the multilayer interfaces with a localized adiabatic heat of 1640° C., thus permanently joining the segments via alloying. It is thus possible to fabricate individualized bone fixation plates out of heat-responsive alloys on demand either in a factory or directly in the hospital.

The exemplary attachment method according to the invention may use any type of welding, including, but not limited to, reactive welding, brazing (e.g., vacuum brazing, etc.), laser welding, electron-beam welding, friction welding, explosive welding, current welding, chromium welding, arc welding and resistance welding to affix the first and second bone plates 102, 104 to one another, wherein the selected welding method is related to a material of the bone plates 102, 104 and any coating(s) provided thereon. For example, a brazing technique may be used to combine the first and second bone plates 102, 104, the brazing heating the coating to a desired temperature to cause welding. Furthermore, vacuum brazing may be used to combine the first and second bone plates 102, 104 to provide a clean, flux-free joint free of oxygen contamination. Specifically, a few micrometers of the surface of the first and second bone plates 102, 104 may be removed by heating in a vacuum or sputtering prior to brazing to remove any oxidized layers, with a depth of the layer removal selected to remove only a portion of the bone plates 102, 104 which may have been penetrated by oxygen, as those skilled in the art will understand. It is respectfully submitted that the removal of oxidized layers may be performed with any of the welding techniques disclosed herein without deviating from the scope of the invention. Once the oxidized layers have been removed, a brazing material may be deposited over select portions of the first and second bone plates. In one embodiment, a Ti-20Zr-20Cu-20Ni braze may be applied between the first and second bone plates 102, 104. The first and second bone plates 102, 104 may then be positioned against one another in a vacuum oven having a vacuum of $1e^{-5}$ or greater at a pressure of approximately 10 kPa. The first and second bone plates 102, 104 may then be heated to approximately 1000° C. for approximately five minutes to form an intermetallic bond therebetween. In another embodiment, the materials for the first and second bone plates 102, 104 may be selected to be less prone to oxidation to bypass the need to remove oxidized layers.

A laser welding technique may be used to weld two bone plate components formed of the same material to one another. For example, a bone fixation system (not shown) may comprise a universal shaft portion configured for placement over a shaft of a long bone. A physician or other user may then select a head portion configured for placement over the head of either a right or left oriented bone. The head and shaft portions may be formed of the same metallic material and positioned adjacent to one another with a pressure of 10 kPa. A pulsed Nd:YAG laser is then aimed parallel to an interface between the first and second portions of the bone plate to weld the surface areas. As those skilled in the art will understand, the selected laser source may be chosen to apply a substantially low thermal stress to a bulk material of the bone plate. The laser weld provides a concentrated heat source, allowing for narrow welds focused on a joint region between the head and shaft, thus permitting welding without excessive heating of the bone fixation system. The above-recited bone fixation system (not shown) may also use electron-beam welding, which also permits a localized welding. Electron-beam welding also provides the advantage of a smaller beam diameter. When working with intermetallic compounds, electron-beam welding melts only a surface of the material. As those skilled in the art will understand, laser welding and electron-beam welding may be performed without providing a coating between first and second portions of a bone fixation system. Friction welding may also be performed in the above-recited bone fixation system, wherein one of the head and the shaft portions may be rotated relative to the other to generate enough heat to cause a fusing of the head and shaft to one another. Friction welding may be used to bond two plate components formed of the same material although it may have limited application in components formed of different materials. In one embodiment, a perpendicular vibration (e.g., 200 Hz; 1 mm. amplitude) may be applied between the plate components to cause friction welding. Current welding may also be used, wherein a current having a predetermined charge is applied to cause the head and shaft to be welded, as those skilled in the art will understand.

Arc welding may be used to bond first and second bone plate components, wherein an electrical discharge is used to liquefy contacting surfaces of the plate components. In limited cases, explosive welding may be used, wherein two or more flat components of a bone plate may be packed with a high-velocity explosive and detonated to compress and melt/plasticize an interface layer of the two sheets. Resistance welding may also be used wherein a heat to form the weld is generated by an electric resistance of the materials of the bone components when subjected to a high electric current, as those skilled in the art will understand.

In another exemplary embodiment of the present invention, bone plate segments configured and dimensioned for distal radius/hand fixation systems may be fashioned to comprise a central segment produced from 316L steel, wherein properties of the 316L steel provide for a high stability for neutralization or compression of a primary bone fracture. The central segment further comprises recesses provided thereover and configured to permit attachment of the central segment to additional side segments (not shown) by means of a free-standing foil (not shown). This configuration allows for the insertion of variable angle screws and K-wires to stabilize fragments in multiple and comminuted fractures or reconstruction of the wrist joint. The free-standing foil is a multilayer stack of, for example, 2000 periods of Ti/Ni, each with a thickness of 40 nm and a 100 µm AuSn solder. Counterpart protrusions featuring the free-standing foils may also be provided and assembled in the hospital according to CT images prior to surgery. The central segment and the counterpart protrusions are ultrasonically cleaned before joining on an ethanol/acetone mixture and loaded at 70 MPa during the joining procedure.

In another exemplary embodiment of the present invention, a bone plate (not shown) is formed from two or more segments. Each segment has one or more contact surfaces arranged thereon to permit reactivity and aid in joining the two or more segments together. For example, a first contact surface on a first segment is shaped to conform to a second contact surface on a second segment. At least one of the first and second contact surfaces has a multilayer as described in greater detail earlier. The bone plate (not shown) is formed by bringing the first contact surface in contact with the second contact surface and igniting the multilayer as described previously. Since the first and second contact surfaces conform to each other in shape, contact therebetween is sufficient to ensure that the bond formed between the first and second segments is strong. The size of the contact surface will depend on the size of the bone plate, but, in an exemplary embodiment, is at least 1 mm$^2$. The contact surface can be any shape as long as the two contacting surfaces can come into close contact with each other. For example, the contact surface can be a straight end of a segment without a recess or protrusion that extends perpendicularly to a longitudinal axis of the segment. In another example, the contact surface can be an edge angled to be oblique relative to a longitudinal axis of the segment. In a further example, the surface can feature one or more steps. The surface can be straight or angled relative to the longitudinal axis of a segment and can be also curvy, wavy, or bumpy. It is further noted that many other variations are also envisioned and lie within the scope of the present invention, as those skilled in the art will understand.

In trauma surgery, there is often a requirement for a greater variability of screw angles for locking plate fixation while still maintaining a mechanically stable lock. Such a variable angle locking mechanism may be formed by depositing multilayer contact patches onto screw holes formed in a bone plate. Screw holes extending through the bone plate are configured and dimensioned so that a sufficient contact area is established therebetween (e.g., by using a hemispherical screw head sunk into a hemispherical bone screw hole). The bone screw holes are coated with a multilayer stack of, for example, 500 Ti/Ni elements, each being approximately 20 nm thick. When the bone plate and bone screws have been successfully positioned in the bone, the bone screw is clamped into the bone screw hole to establish a sufficient contact pressure of approximately 50 to 100 MPa. The multilayer stack is then ignited by an electrical pulse, welding the bone screw to the bone plate. The bone screw and bone plate may be fractured to enable removal thereof from the bone.

The exemplary welding techniques according to the invention ensure a secure connection between first and second bone plates 102, 104 and/or between proximal and distal nail portions 206, 208, preventing any movement of the components relative to one another after implantation. Convention devices have used mechanical connections between separate plate components which often wear down over time, causing friction between the components which may lead to galvanic corrosion. The welding techniques according to the present invention eliminates this frictional movement of the components relative to one another.

The exemplary systems according to the present invention may be manufactured as a kit. The kit may comprise two or more separate bone plate segments that may be attached to one another pre-operatively (e.g., in an operating room) to conform to the requirements of a particular bone fixation procedure. The kit may also comprise instructions with regard to the exemplary welding techniques disclosed herein Although the invention and its advantages have been described in detail, it should be understood that various changes, substitutions, and alterations can be made herein without departing from the spirit and scope of the invention as defined by the appended claims. Moreover, the scope of the present application is not intended to be limited to the particular embodiments of the process, machine, manufacture, and composition of matter, means, methods and steps described in the specification. As one of ordinary skill in the art will readily appreciate from the disclosure of the present invention, processes, machines, manufacture, composition of matter, means, methods, or steps, presently existing or later to be developed that perform substantially the same function or achieve substantially the same result as the corresponding embodiments described herein may be utilized according to the present invention.

It will be appreciated by those skilled in the art that various modifications and alterations of the invention can be made without departing from the broad scope of the appended claims. Some of these have been discussed above and others will be apparent to those skilled in the art.

What is claimed is:

1. A kit for forming a bone plate, comprising:
   a first implant segment formed of a first material;
   a second implant segment formed of a second material; and
   a plurality of layers of an intermetallic material disposed between the first and second segments;
   wherein the first and second implant segments are configured to be metallurgically welded to one another.

2. The kit of claim 1, wherein the first implant segment extends from a first end to a second end and includes a bone-contacting surface and an upper surface and wherein the second implant segment extends from a third end to a fourth end and includes a bone-contacting surface and an upper surface, the plurality of layers being disposed between the second end of the first implant segment and the third end of the second implant segment.

3. The kit of claim 2, wherein the plurality of layers are formed on one of the second end and the third end.

4. The kit of claim 2, wherein the plurality of layers are formed on both the second end and the third end.

5. The kit of claim 2, wherein the first material has a first rigidity and wherein a rigidity of at least one of the second implant segments is lower than the first rigidity.

6. The kit of claim 1, wherein the first material is different from the second material.

7. The kit of claim 1, wherein the plurality of layers of the intermetallic material are formed to produce a negative heat of mixing and wherein at least a portion of at least one of the first and second segments is coated with the plurality of layers of the intermetallic material.

8. The kit of claim 1, wherein the intermetallic material is chosen from the group consisting of Ti/Al, Ni/Al, Ti/Si, Zr/Al, Ti/N and Ti5Si3.

9. A kit for bone fixation, comprising:
   a first bone implant segment formed of a first material;
   a second bone implant segment formed of a second material; and
   a plurality of layers of an intermetallic material disposed between the first and second segments;

wherein the first and second implant segments are configured to be metallurgically welded to one another to form a hybrid bone plate.

10. The kit of claim 9, further comprising instructions for metallurgically welding the first and second bone implant segments to one another.

11. The kit of claim 9, wherein the plurality of layers of the intermetallic material are formed to produce a negative heat of mixing.

12. The kit of claim 9, wherein the first and second bone segments are each formed of a different material.

13. The kit claim 9, wherein the plurality of layers are deposited over one of the first and second materials of the surgical implant.

14. A kit for forming a bone plate, comprising:
a first implant segment formed of a first material;
a plurality of second implant segments, each being formed of a material different than the first material, each of the second implant segments being configured to provide one of a different configuration and a different material property to a hybrid bone plate formed when joined to the first implant segment;
a plurality of layers of an intermetallic material disposed between the first implant segment and a selected one of the second implant segments at a joint at which the first implant segment and the selected one of the second implant segments are metallurgically welded to one another to form a hybrid bone plate.

* * * * *